United States Patent [19]

D'Silva

[11] 4,066,689

[45] Jan. 3, 1978

[54] KETOALKANESULFENYLCARBAMOYL AND KETOALKANETHIOSULFENYLCARBAMOYL HALIDES

[75] Inventor: Themistocles D. J. D'Silva, South Charleston, W. Va.

[73] Assignee: Union Carbide Corporation, New York, N.Y.

[21] Appl. No.: 688,223

[22] Filed: May 20, 1976

[51] Int. Cl.$^2$ .................. C07C 125/00; C07C 125/03
[52] U.S. Cl. .................................. 260/544 C; 560/16; 560/145; 560/147; 560/134; 560/148
[58] Field of Search ............... 260/544 C, 470, 479 R, 260/479 S, 481 R, 479 C, 481 C

[56] References Cited

U.S. PATENT DOCUMENTS

| | | | |
|---|---|---|---|
| 2,894,013 | 7/1959 | Werres | 260/544 C |
| 3,152,175 | 10/1964 | Ottenheym et al. | 260/544 C |
| 3,301,894 | 1/1967 | Ottmann et al. | 260/544 C |
| 3,699,163 | 10/1972 | Kohn | 260/544 C |
| 3,699,167 | 10/1972 | Kaiser | 71/121 |
| 3,879,190 | 4/1975 | Fuchs | 260/544 C |
| 3,925,368 | 12/1975 | Cooper et al. | 260/544 C |
| 3,954,836 | 5/1976 | Siegle et al. | 260/544 C |
| 3,962,327 | 6/1976 | Schlee et al. | 260/544 C |
| 3,991,093 | 11/1976 | Koenig et al. | 260/544 C |

*Primary Examiner*—Norman Morgenstern
*Attorney, Agent, or Firm*—Richard C. Stewart

[57] ABSTRACT

Ketoalkanesulfenylcarbamoyl and ketoalkanethiosulfenylcarbamoyl halides are useful intermediates in the preparation of pesticidally active carbamates.

20 Claims, No Drawings

KETOALKANESULFENYLCARBAMOYL AND KETOALKANETHIOSULFENYLCARBAMOYL HALIDES

The invention relates to novel ketoalkanesulfenylcarbamoyl and ketoalkanethiosulfenylcarbamoyl halides compounds and to their preparation.

More particularly, this invention relates to novel compounds of the following general formula:

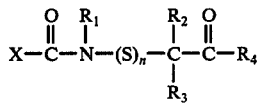

wherein:
$R_1$ is alkyl;
$R_2$ is alkyl or chlorine;
$R_3$ is hydrogen, alkyl, phenyl, alkoxycarbonyl, alkanoyl or phenoxycarbonyl;
$R_4$ is hydrogen, alkyl, phenoxy, alkoxy, phenyl, or $R_3$ and $R_4$ together may form an alkylene chain completing a five or six membered alicyclic ketone or dione;
$n$ is 1 or 2;
X is chlorine or fluorine.

$R_1$, $R_2$, $R_3$, and $R_4$ individually may not include more than 6 aliphatic carbons. The preferred compounds of this invention are those in which $R_1$ is methyl and in which the total number of aliphatic carbons included in $R_2$, $R_3$, and $R_4$ individually does not exceed four.

Carbamoyl halides compounds of this invention are useful intermediates in the preparation of nematocidally, insecticidally and miticidally active carbamate compounds. For example, 1-isopropylthioacetaldoxime can be reacted with N-methyl-N-(2,4-dimethyl-3-oxo-2-pentanethiosulfenyl) carbamoyl fluoride in the presence of an acid acceptor such as triethylamine to produce 1-isopropylthioacetaldehyde-0-[N-methyl-N-(2,4-dimethyl-3-oxo-2-pentanethiosulfenyl) carbamoyl] oxime, the corresponding pesticidally active carbamate. The above disclosed reactions are described in more detail in my copending U.S. patent application Ser. No. 688,410 entitled Ketoalkanesulfenyl and Ketoalkanethiosulfenyl Carbamates filed concurrently herewith.

Carbamoyl halide compounds of this invention can be prepared according to a variety of methods, the choice of method being influenced to a large extent by the value of $n$ and by X. For example, one preferred method of preparing novel ketoalkanesulfenylcarbamoyl halide compounds is by the process shown in the following reaction scheme:

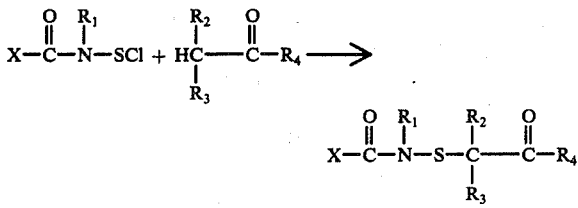

Alpha-chloroketoalkanesulfenylcarbamoyl halide compounds of this invention can be prepared as illustrated in the following general reaction scheme:

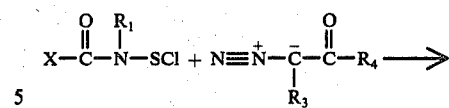

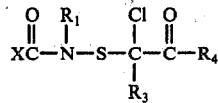

Ketoalkanethiosulfenylcarbamoyl chloride compounds of this invention can be prepared in accordance with the following general reaction scheme:

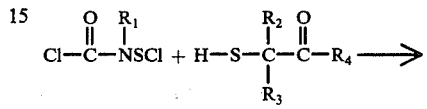

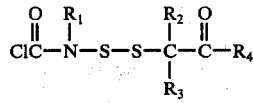

In each of the above general reaction schemes $R_1$, $R_2$, $R_3$, $R_4$ and X are as described above.

Essentially equivalent amounts of the reactants are reacted either neat or in an inert solvent. Any inert solvent such as chloroform, tetrahydrofuran, benzene, dioxane or the like may be used.

Reaction temperatures are not critical and will tend to vary from about $-30°$ C to about $100°$ C, depending to a large extent on the reactivity and stability of the reactants.

Reaction pressures are not critical. The reaction is usually conducted at atmospheric or autogenous pressure.

Generally, the reactions are exothermic. External cooling may be required in order to maintain the reaction temperature within acceptable limits.

Ketoalkanethiosulfenylcarbamoyl fluoride compounds of this invention can be conveniently prepared according to the following reaction scheme:

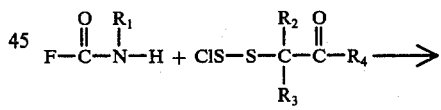

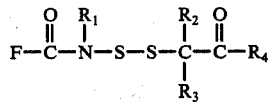

In the above reaction scheme $R_1$, $R_2$, $R_3$ and $R_4$ are as described above. Essentially, equivalent amounts of the reactants are contacted in the presence of an acid acceptor. The reaction is usually conducted in an inert solvent. Any inert solvent may be used such as benzene, toluene, xylene, dioxane, tetrahydrofuran, ethyl ether, methylene chloride and the like. The acid acceptor can be either an organic or an inorganic base. Suitable inorganic bases include alkali metal hydroxides such as sodium or potassium hydroxide. When an inorganic base is employed as an acid acceptor in an organic solvent, the reaction can be conducted in either a mixture of liquid-solid phases, or a two-liquid phase system in which the reactants are dissolved in the organic phase and the inorganic base is dissolved in the aqueous phase. In the former case, phase transfer agents such as crown ethers and in the latter case agents such as quaternary ammonium halides can be used to facilitate the transfer of the reactants across the interface. The organic bases which are useful as acceptors include tertiary amines, such as triethylamine, 1,4-diazabicyclo [2.2.2] octane, pyridine or the like.

Reaction temperatures and pressures are not critical. The reaction goes essentially to completion at ambient temperature. If shorter reaction times are desired elevated temperatures may be used. The reaction is usually conducted at atmospheric or autogenous pressure.

Ketoalkanethiosulfenyl chloride precursors used in the preparation of the novel ketoalkanethiosulfenylcarbamoyl fluorides of this invention can be conveniently prepared by the methods disclosed in R. C. Fuson et al. J. Org. Chem. 11, 469 (1946) and I. T. Kay et al J. Chem. Soc. [C], 445 (1970). Mono substituted carbamic acid fluoride precursors can be prepared according to the method disclosed in U.S. Pat. No. 3,639,471.

N-Chlorothiocarbamoyl chloride precursors can be prepared according to the methods described in U.S. Pat. No. 3,699,167. N-Chlorothiocarbamoyl fluoride precursors can be prepared according to the methods described in German Pat. Nos. 1,931,054 and 2,023,079.

Diazo keto precursors can be conveniently prepared according to conventional methods, as for example the methods described in Tetrahedron Letters, 2285 (1964), *Org. Synthesis* Vol. IV page 424 and references cited therein.

The following specific examples are presented to particularly illustrate the manner in which the novel compounds of this invention can be prepared.

EXAMPLE I

Preparation of
N-Methyl-N-(2,4-dimethyl-3-oxo-2-pentane sulfenyl)carbamoyl chloride N-Methyl-N-chlorothiocarbamoyl chloride (3.2 g, 0.02 m) was added to 2.28g (0.02m) of diisopropyl ketone. The spontaneous exotherm raised the temperature to 35° C. After standing for 1 hour the dissolved hydrogen chloride gas was removed by warming the mixture under reduced pressure. Weight of the residual oil 4.0g. $ND^{23}1.4947$.

Infra-red (Neat) 5.82, 5.92μ(carbonyl).
NMR(CDCl$_3$)δ 1.15 (d), J=7.0 H$_Z$, 6H; 1.55 (s), 6H; 3.22 (s), 3H; 3.0–3.5 (m), 1H.

EXAMPLE II

Preparation of
N-Methyl-N-(2-formyl-2-propanesulfenyl)carbamoyl chloride

A solution of 1.6g(0.01m) N-Methyl-N-chlorothiocarbamoyl chloride in 20 ml of methylene chloride was added to a solution of 1.5g(0.01m) of isobutyraldehyde and the reaction mixture heated to 35° C for 0.5 hr. The solvent was removed under reduced pressure to yield 1.7g of an yellow oil.

Infra-red (Neat) 5.82μ(C═O).
NMR(CDCl$_3$)δ 1.41 (s), 6H; 3.37 (s), 3H, 9.45 (s), 1H.

EXAMPLE III

Preparation of
N-Methyl-N-(3-formyl-3-pentanesulfenyl)carbamoyl chloride

A solution of 1.6g(0.01m) N-Methyl-N-chlorothiocarbamoyl chloride in 25 ml of methylene chloride was added dropwise to a stirred solution of 2.2g(0.022m) of 2-ethylbutyraldehyde in 25 ml of methylene chloride. The mixture was warmed to 40° C for 2 hrs. After the evolution of hydrogen chloride had ceased, the solvent was removed under vacuum to yield 2.19g of an oil.

Infra-red (Neat) 5.85μ (C═O).
NMR(CDCl$_3$) δ 0.95 (t), J=7.0 H$_z$, 6H; 1.75 (m). J=7.0 H$_Z$, 4H; 3.36 (s), 3H; 9.49 (s), 1H.

EXAMPLE IV

Preparation of
N-Methyl-N-(3-formyl-3-heptanesulfenyl)carbamoyl chloride

N-Methyl-N-chlorothiocarbamoyl chloride (1.6g, 0.01m) was added to 1.28g(0.01m) of 2-ethylhexaldehyde. The spontaneous exotherm raised the temperature of the mixture from 24° C, to 32° C, with evoluation of hydrogen chloride. After stirring for 1 hour the dissolved gas was removed under reduced pressure to yield 2.4g of a residual oil.

Infra-red (Neat) 5.8 (C═O)μ.
NMR (CDCl$_3$) δ 1.0 (t). J=7.0 H$_Z$, 6H; 1.0–2.0 (m), 8H 3.34 (s), 3H; 9.47 (s), 1H.

EXAMPLE V

Preparation of
N-Methyl-N-(1-chloro-2-formyl-2-propanesulfenyl)carbamoyl chloride N-Methyl-N-chlorothiocarbamoyl chloride (8.0g, 0.05m) was added dropwise at 5° C to 10° C to 3.89g(0.05m) of methacrolein over a period of 10 minutes. After stirring for 1 hour the reaction mixture was kept under vacuum to remove volatile materials. Weight of the residual oil 10.8g.

Infra-red (Neat) 5.9(C=O)μ

NMR (CDCl₃) δ 1.46 (s), 3H; 3.40 (s), 3H; 3.87 (d), $J_{AB}$=12.0 Hz and 4.08 (d). $J_{BA}$=12.0 Hz, 2H; 9.52 (s), 1H.

EXAMPLE VI

Preparation of N-Methyl-N-(2-benzoyl-2-propanesulfenyl)carbamoyl chloride

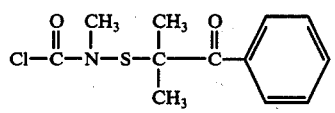

A mixture of 14.8g (0.1m) of isobutyrophenone and 16.0g (0.1m) of N-methyl-N-chlorothiocarbamoyl chloride was heated slowly to 30° C whilst stirring. The exothermic reaction raised the temperature to 42° C with evolution of hydrogen chloride. After stirring for 0.5 hours at 40° C, the residual hydrochloric acid was removed under reduced pressure. Weight of the residual oil 27.0g.

Infra-red (Neat) 5.78, 5.98μ(C=O).

NMR (CDCl₃) δ 1.6 (s), 6H; 3.30 (s), 3H; 7.3–8.1 (m) 5 H.

EXAMPLE VII

Preparation of N-Methyl-N-(2-methyl-1-oxo-2-cyclopentanesulfenyl)-carbamoyl chloride

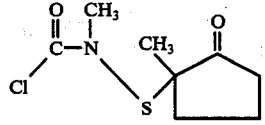

To a solution of 4.8g(0.05m) of 2-methylcyclopentanone in 100 ml of methylene chloride cooled to 10° C was added dropwise with stirring 8.0g(0.05m) of N-Methyl-N-chlorothiocarbamoyl chloride over a period of 10 min. After stirring at 15° C for 0.5 hours, the solvent was removed under reduced pressure to yield 10.0g of a residual oil.

Infra-red (Neat 5.8)μ(C=O).

NMR (CDCl₃) δ 1.53 (s), 3H; 1.9–2.7 (m), 6H; 3.38, (s) 3H.

EXAMPLE VIII

Preparation of N-Methyl-N-(1-carboethoxy-1-chloromethanesulfenyl)carbamoyl chloride

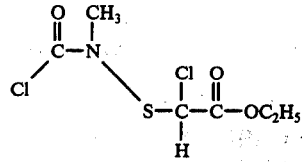

To a solution of 2.35g(0.02m) of ethyldiazoacetate in 50 ml of anhydrous ethyl ether, cooled to −10° C, was added dropwise with stirring 3.2g(0.02m) of N-methyl-N-chlorothiocarbamoyl chloride dissolved in 25 ml of ethyl ether, over a period of 15 min. After stirring for an additional 45 minutes and the evolution of nitrogen had ceased, the solvent was removed under reduced pressure to yield 4.8g of an oil.

Infra-red (Neat) 5.8μ(C=O).

NMR(CDCl₃) δ 1.35 (t), J=7.0Hz, 3H; 3.55 (s), 3H; 4.33 (q), J=7.0 Hz, 2H; 5.62 (s), 1H.

EXAMPLE IX

Preparation of N-Methyl-N-(bis-ethoxycarbonyl-chloromethane-sulfenyl)carbamoyl chloride

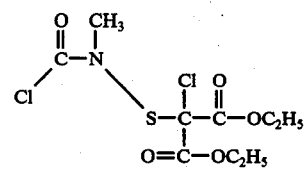

N-methyl-N-chlorothiocarbamoyl chloride (3.2g,0.02m) was added dropwise with stirring to 3.72g(0.02m) of ethyldiazomalonate. The spontaneous exotherm raised the temperature of the reaction misture from 25° C to 29° C with evolution of gas. The mixture was stirred an additional 20 hours at 30° C. Weight of the crude oil product 5.0g.

Infra-red (Neat) 5.85 (with shoulder)(C=O)μ.

NMR(CDCl₃) δ 1.34 (t), J=7.0 Hz, 6H; 3.53 (s), 3H; 4.35 (q), J=7.0 Hz, 4H.

EXAMPLE X

Preparation of N-Methyl-N-(2,4-dimethyl-3-oxo-2-pentanesulfenyl)-carbamoyl fluoride

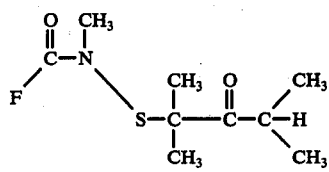

N-methyl-N-chlorothiocarbamoyl fluoride (1.43g,0.01m) was added to a solution of 1.4g(0.01m) of 2,4-dimethyl-3-pentanone in 25 ml of methylene chloride. There was no immediate exotherm. The solvent was removed by blowing nitrogen. After an induction period of about 5 minutes there was a spontaneous evolution of hydrogen chloride. After standing for 1 hour the residual gas was removed under reduced pressure. Weight of the product 2.47g.

$N_D24$ 1.4730.

Intra-red (Neat 5.58, 5.87μ(C=O).

NMR(CDCl₃) δ 1.13 (d), J=7.0 Hz, 6H; 1.5 (s), 6H; 2.9–3.5 (m), 1H; 3.23 (d), J=1.0 Hz, 3H.

EXAMPLE XI

Preparation of N-Methyl-N-(2-methyl-1-oxo-2-cyclopentanesulfenyl)-carbamoyl fluoride

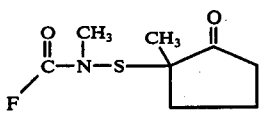

N-methyl-N-chlorothiocarbamoyl fluoride (1.43g,0.01m) was added dropwise to a solution of 0.98g(0.01m) of 2-methylcyclopentanone in 25 ml of methylene chloride. After 2 hrs. when hydrogen chloride has ceased to evolve the residual gas was removed under reduced pressure to give 1.95g of product, $N_D^{25} 1.4893$.

Infra-red (Neat) 5.56, 5.75μ(C=O).

NMR(CDCl$_3$) δ 1.47 (s), 3H; 1.9–2.8 (m), 6H; 3.29 (d), J=1.0 H$_z$, 3H.

EXAMPLE XII

Preparation of N-Methyl-N-(2,4-dimethyl-3-oxo-2-pentanethiosulfenyl)carbamoyl fluoride

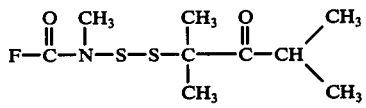

Sulfur monochloride 33.78g(0.25m) was added dropwise to a stirred solution of 28.5g(0.25m) of diisopropyl ketone in 150 ml of methylene chloride. The exothermic reaction raised the temperature to 40° C. The addition of sulf r monochloride was completed in 0.5 hours. The reaction mixture was stirred for another 3 hours at 40° C and the solvent removed to yield 48.6g of 2,4-dimethyl-3-oxo-2 pentanethiosulfenyl chloride.

In a separate polypropylene reactor, 13.03g (0.228m) of methyl isocyanate was added dropwise to a stirred mixture of 4.57g(0.228m) hydrogen fluoride in 250 ml of toluene at −60° C over the period of 12 minutes. After stirring the mixture at 0° C for 1 hour, 48.6g(0.228m) of 2,4-dimethyl-3-oxo-2-pentanethiosulfenyl chloride was added followed by the slow addition of 23.1g(0.228m) of triethylamine, whilst the temperature was maintained between 10°–20° C. The reaction mixture was stirred for another 50 minutes at 20°–24° C and then diluted with 100 ml of water and agitated. The toluene layer was separated and dried over magnesium sulfate. Removal of the solvent under reduced pressure yielded 50.8g of a light yellow oil.

$N_D^{24} 1,5081$.

Intra-red (Neat) 5.55, 5.84μ(C=O).

NMR(CDCl$_3$) δ 1.07 (d), J=7.0 H$_z$, 6H; 1.61 (s), 6H; 3.0–3.5 (m), 1H; 3.22 (d), J=1.0 H$_z$, 3H.

EXAMPLE XIII

Preparation of N-Methyl-N-(2-formyl-2-propanethiosulfenyl)carbamoyl fluoride

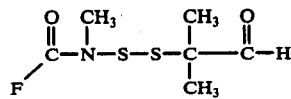

Isobutyraldehyde (36.0g,0.5m) was added dropwise to a solution of 67.5g(0.5m) of sulfur monochloride in 250 ml of methylene chloride. The mixture was stirred at 30° C for 45 minutes till the evolution of hydrogen chloride had ceased. Removal of the solvent under reduced pressure yielded 85.5g of 2-formyl-2-propanethiosulfenyl chloride as a light yellow oil.

In a separate polypropylene reactor, 28.52g (0.5m) of methyl isocyanate was added over a period of 15 minutes under nitrogen, to a mixture of 10g(0.5m) of anhydrous hydrogen fluoride in 150 ml of methylene chloride cooled to −10° C. After stirring for 45 minutes, 85.5g(0.5m) of 2-formyl-2-propanethiosulfenyl chloride was added rapidly to the reactor followed by the slow addition of 50.6g(0.5m) of triethylamine whilst maintaining the temperature at −10° C. The mixture was stirred for 2 hours and the temperature was allowed to rise to room temperature. The salt formed was washed with (3×200 ml) of water and the organic phase was dried and concentrated. Distillation yielded 32.67 g of the product b.p. 79°–80° C/0.5mm. $N_D^{24}$ 1.5132

Infra-red (Neat) 5.55, 5.78μ(C=O).

NMR(CDCl$_3$)δ1.53 (s), 6H; 3.22 (d) J=1.0 H$_z$, 3H; 9.73 (s), 1H.

EXAMPLE XIV

Preparation of 1-[N-Methyl-N-(2,4-dimethyl-3-oxo-2-pentanesulfenyl) carbamoyloxy]-napthalene

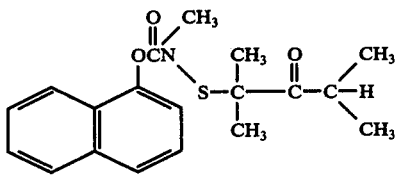

To a solution of 10.0g(0.042m) of N-methyl-N-(2,4-dimethyl-3-oxo-2-pentanesulfenyl)carbamoyl chloride and 6.06g(0.042m) of 1-naphthol in 75 ml of dioxane was added 4.26g(0.042m) of triethylamine. After stirring at room temperature for 17 hours the reaction mixture was diluted with 500 ml of cold water and the product taken into ethyl acetate. The organic phase was washed in turn with 1.0 percent sodium hydroxide and water and then dried over magnesium sulfate. On removal of the solvent it yielded 9.4g of a residual oil.

Infra-red (Neat) 5.8, 5.88μ (Shoulder) C=O.

NMR(CDCl$_3$) δ1.0, (d) J=7.0 H$_z$, 6H, 1.41 (s), 6H 3.30 (s), 3H; 7.2–8.1 (m), 7H.

Calc'd for $C_{19}H_{23}NO_3S$: C, 66.06; H, 6.71; N, 4.05. Found: C, 65.25; H, 6.28; N, 4.03.

EXAMPLE XV

Preparation of 1-Methylthioacetaldehyde O-[N-methyl-N-(2,4-dimethyl-3-oxo-2-pentanethiosulfenyl)carbamoyl]oxime

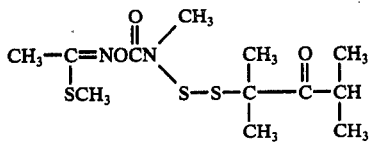

To a solution of 5.0g(0.0476m) of 1-methylthioacetaldoxime and 12.01g(0.0476m) of N-methyl-N-(2,4-dimethyl-3-oxo-2-pentanethiosulfenyl)carbamoyl fluoride in 75 ml of dioxane, was added 4.8g(0.0476m) of triethylamine. After stirring at room temperature for 18 hours the reaction mixture was diluted with 100 ml of water and the product was extracted in ethyl acetate. The organic extract was washed in turn with aqueous soduium bicarbonate solution and water. Dried over magnesium sulfate and concentrated, the product crystallized from isopropylether and hexane solution to yield 8.1g of a white solid. m.p. 74°-75° C.

Calc'd. for $C_{12}H_{22}N_2O_3S_2$: C, 42.57; H, 6.55; N, 8.28. Found: C, 42.71; H, 6.64; N, 8.29.

EXAMPLE XVI

Preparation of 1-Methylthioacetaldehyde O-[N-methyl-N-(2-benzoyl-2-propanethiosulfenyl)carbamoyl]oxime.

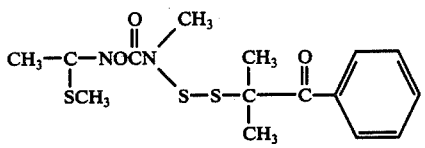

Prepared as in Example XV by reacting 10.5g (0.1m) of 1-methylthioacetaldoxime, 28.74g (0.1m) of N-methyl-N-(2-benzoyl-2-propanethiosulfenyl)carbamoyl fluoride and 10.19g (0.1m) of triethylamine in 100 ml of dioxane. Yield 9.48g of white solid. m.p. 80°-82° C.

Calc'd. for $C_{15}H_{20}N_2O_3S_3$: C, 48.36; H, 5.41; N, 7.52. Found: C, 48.34; H, 5.67; N, 7.44.

EXAMPLE XVII

Preparation of 2-[[O-[N-Methyl-N-(2-methyl-1-oxo-2-cyclopentanesulfenyl)carbamoyl]oximino]]-3,5,5-trimethylthiazolidin-4-one

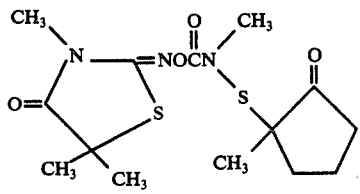

To a solution of 3.93g 0.0225m) of 3,5,5-trimethyl-2-oximino-thiazolidin-4-one and 2.28g (0.0225m) of triethylamine in 75 ml of dioxane was added dropwise with stirring 5.0g (0.0225m) of N-methyl-N-(2-methyl-1-oxo-2-cyclopentanesulfenyl)carbamoyl chloride whilst maintaining the temperature between 10°-15° C. The reaction mixture was left standing for 16 hours at 5° C, and then diluted with ice water. The product was extracted in ethylacetate, dried and concentrated to yield 0.66g of white solid, m.p. 119°-121° C.

Calc'd. for $C_{14}H_{21}N_3O_4S_2$: C, 46.77; H, 5.89; N, 11.69. Found: C, 46.35; H, 5.88; N, 11.42.

EXAMPLE XVIII

Preparation of 2[[O-[N-Methyl-N-(2-benzoyl-2-propanesulfenyl)carbamoyl]oximino] -3,5,5-trimethylthiazolidin-4-one

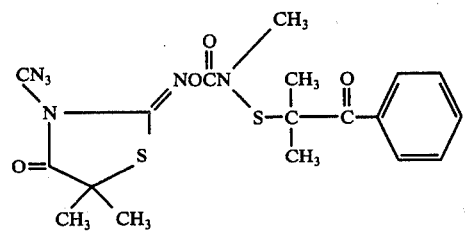

To a solution of 2.5g (0.015m) of 3,5,5-trimethyl-2-oximino-thiazolidin-4-one and 3.93g (0.015m) of N-methyl-N-(2-benzoyl-2-propanesulfenyl)carbamoyl chloride in 100 ml of dioxane was added 1.5g (0.015m) of triethylamine. After stirring at room temperature for 16 hours, the reaction mixture was diluted with water and the product isolated in ethylacetate. Recrystallized from isopropyl ether. Weight of the product 1.3g, m.p. 98°-100° C.

Calc'd. for $C_{18}H_{23}N_3O_4S_2$: C, 52.79; H, 5.66; N, 10.26. Found: C, 52.05; H, 5.59; N, 10.59.

EXAMPLE XIX

Preparation of 2-[[O-[N-Methyl-N-(3-formyl-3-pentanesulfenyl)carbamoyl]oximino]]-3,5,5-trimethylthiazolidin -4-one

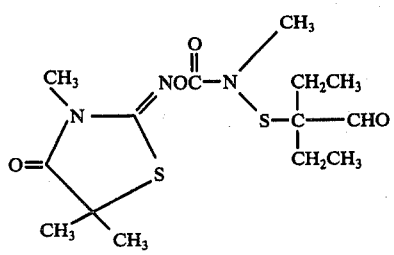

To a solution of 8.7g (0.05m) of 3,5,5-trimethyl-2-oximinothiazolidin-4-one and 8.9g (0.05m) of a 90 percent solution of N-methyl-N-(3-fromly-3-pentanesulfenyl)carbamonyl chloride in 150 ml of dioxane was added 5.04g (0.05m) of triethylamine. The reaction mixture was stirred at room temperature for 90 hours, and added 300 ml of cold water. The solid formed was collected and taken in isopropyl ether and chloroform and chilled. Weight of the solid precipitate 3.5g. Analytical sample, m.p. 105°-106° C.

Calc'd. for $C_{14}H_{23}N_3O_4S_2$: C, 46.52; H, 6.41; N, 11.62. Found: C, 46.81; H, 6.11; N, 11.67.

EXAMPLE XX

Preparation of
2-[[O-[N-Methyl-N-(bis-ethoxycarbonylchloromethanesulfenyl)carbamoyl]oximino]]-3,5,5-trimethyl-thiazolidin-4-one

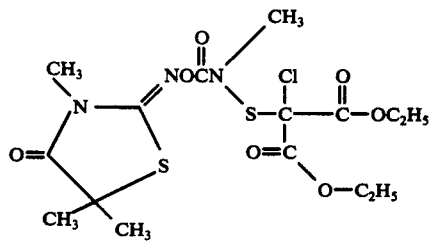

A mixture of 1.91g (0.011m) of 3,5,5-trimethyl-2-oximinothiazolidin-4-one, 5.0g (0.011m) of a 70 percent solution of N-methyl-N-(bis-ethoxycarbonylchloromethanesulfenyl) carbamoyl chloride and 1.11g (0.011m) of triethylamine in 100 ml of dioxane was stirred overnight at room temperature. The reaction mixture was diluted with water, the product was extracted into ethylacetate and the organic phase was washed with water, and dried over magnesium sulfate. Removal of the solvent gave a residual oil which was purified by chromatography through silica gel.

IR (Neat) 5.9μ (C=O).

NMR(CDCl$_3$) δ 1.36 (t), J=7.0Hz, 6H; 1.68 (s), 6H; 3.29 (s) 3H; 3.46 (s) 3H; 4.36 (q), J-7.0Hz, 4H.

The following compounds are representative of the other compounds that are within the scope of this invention which can be prepared according to this invention by selecting appropriate starting materials for use in the procedures described herein above.

N-Methyl-N-(2,4,4-trimethyl-3-oxo-2-pentanesulfenyl) carbamoyl fluoride.
N-Methyl-N-(bis-ethoxycarbonylchloromethanesulfenyl) carbamoyl fluoride.
N-Methyl-N-(2,6,6-trimethyl-1-oxo-2-cyclohexanesulfenyl) carbamoyl chloride.
N-Hexyl-N-(2-benzoyl-2-propanesulfenyl)carbamoyl fluoride.
N-Methyl-N-(2,6,6-trimethyl-1-oxo-2-cyclohexanesulfenyl) carbamoyl fluoride.
N-Methyl-N-(2-formyl-2-propanesulfenyl)carbamoyl fluoride.
N-Methyl-N-(1-carboethoxy-1-chloromethanesulfenyl) carbamoyl fluoride.
N-Methyl-N-(1-chloro-2-formyl-2-propanesulfenyl)carbamoyl fluoride.
N-Methyl-N-(3-formyl-3-pentanesulfenyl)carbamoyl fluoride.
N-Methyl-N-(2,4,4-trimethyl-3-oxo-2-pentanethiosulfenyl) carbamoyl fluoride.
N-Pentyl-N-(2,6-dimethyl-1-oxo-2-cyclohexanethiosulfenyl) carbamoyl fluoride.
N-Methyl-N-(2-benzoyl-2-hexanethiosulfenyl)carbamoyl fluoride.
N-Methyl-N-(2-formyl-2-propanethiosulfenyl)carbamoyl fluoride.
N-Methyl-N-(1-chloro-2-formyl-2-propanethiosulfenyl) carbamoyl fluoride.
N-Methyl-N-(3-formyl-3-pentanethiosulfenyl)carbamoyl fluoride.
N-Methyl-N-(2,4,4-trimethyl-3-oxo-2-octanesulfenyl) carbonyl fluoride.
N-Butyl-N-(2-hexyl-1-oxo-2-cyclohexylsulfenyl)carbamoyl Chloride.
N-Butyl-N-(2,4,4-trimethyl-3-oxo-2-pentanesulfenyl) carbamoyl chloride.
N-(tert-Butyl-N-(1-chloro-2-formyl-2-propanethiosulfenyl) carbamoyl fluoride.
N-Ethyl-N-(3-hexanoyl-3-pentanesulfenyl)carbamoyl chloride.
N-Isopropyl-N-(2,4-dimethyl-3-oxo-2-propanethiosulfenyl) carbamoyl fluoride.
N-Ethyl-N-(2-chloro-2-butanesulfenyl)carbamoyl chloride.
N-Propyl-N-(2-phenoxycarbonyl-2-propanesulfenyl)-carbamoyl chloride.
N-Methyl-N-(1-carboethoxy-1-chloromethanesulfenyl) carbamoyl fluoride.
N-Butyl-N-(1-chloro-1-formyl-1-carbobutoxy-methane sulfenyl)carbamoyl chloride.
N-Butyl-N-(2-acetyl-3-oxo-4-methyl-2-pentanesulfenyl) Carbamoyl Chloride.
N-Isopropyl-N-(1-chloro-2-formyl-2-propanesulfenyl)-carbamoyl chloride.
N-Methyl-N-(2-chloro-5,5-dimethyl-1,3-dioxo-2-cyclohexanesulfenyl)carbamoyl chloride.

What is claimed is:

1. A compound of the formula:

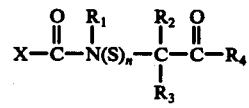

wherein:
$R_1$ is alkyl;
$R_2$ is alkyl or chlorine;
$R_3$ is hydrogen, alkyl, phenyl, alkoxycarbonyl, alkanoyl or phenoxycarbonyl;
$R_4$ is hydrogen, alkyl, phenoxy, alkoxy or phenyl or $R_3$ and $R_4$ together may form as alkylene chain completing a five or six membered alicyclic ketone or dione;
$n$ is 1 or 2;
X is chlorine or fluorine;
wherein $R_1$, $R_2$, $R_3$ and $R_4$ substituents individually may not include more than 6 aliphatic carbons.

2. A compound of the formula

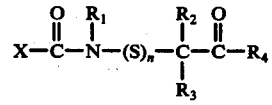

wherein:
$R_1$ is alkyl;
$R_2$ is alkyl or chlorine;
$R_3$ is hydrogen, alkyl, phenyl or alkanoyl;
$R_4$ is hydrogen, alkyl or phenyl or $R_3$ and $R_4$ together may form an alkylene chain completing a five or six membered alicyclic ketone or dione;
$n$ is 1 or 2;
$X$ is chlorine or fluorine; with the proviso that $R_1$, $R_2$, $R_3$ and $R_4$ substituents individually may not include more than six aliphatic carbon atoms.

3. A compound according to claim 2 wherein X is fluorine.

4. A compound according to claim 2 wherein X is chlorine.

5. A compound according to claim 2 wherein $R_1$ is alkyl having from 1 to 4 carbons.

6. A compound according to claim 2 wherein $R_1$ is methyl.

7. A compound according to claim 2 wherein $R_3$ is alkyl having from 1 to 4 carbons.

8. A compound according to claim 2 wherein $R_3$ is phenyl.

9. A compound according to claim 2 wherein $R_4$ is alkyl having 1 to 4 carbons.

10. A compound according to claim 2 wherein $R_4$ is phenyl.

11. A compound according to claim 2 wherein $R_1$, $R_3$ and $R_4$ are individually alkyl having from 1 to 4 carbons.

12. A compound according to claim 2 wherein $R_2$ is alkyl having from 1 to 4 carbons.

13. A compound according to claim 2 wherein $R_2$ is methyl.

14. A compound according to claim 2 wherein $R_2$ is chlorine.

15. A compound according to claim 2 wherein $R_3$ is methyl.

16. A compound according to claim 2 wherein $R_4$ is isopropyl.

17. N-Methyl-N-(2,4-dimethyl-3-oxo-2-pentanesulfenyl) carbamoyl chloride.

18. N-Methyl-N-(2-benzoyl-2-propanesulfenyl)carbamoyl chloride.

19. N-Methyl-N-(2,4-dimethyl-3-oxo-2-pentanesulfenyl) carbamoyl fluoride.

20. N-Methyl-N-(2,4-dimethyl-3-oxo-2-pentanethiosulfenyl) carbamoyl fluoride.

* * * * *

UNITED STATES PATENT OFFICE
CERTIFICATE OF CORRECTION

Patent No. 4,066,689                 Dated January 3, 1978

Inventor(s) Themistocles D.J. D'Silva

It is certified that error appears in the above-identified patent and that said Letters Patent are hereby corrected as shown below:

Column 6, line 32, which reads, "...misture" should read --...mixture--

Column 6, line 55, which reads, "1.4g" should read --1.14g--

Column 6, line 66, which reads, "Intra-red" should read --Infra-red--

Column 7, line 42, which reads, "sulf r" should read --sulfur--

Column 7, line 65, which reads, "Intra-red" should --Infra-red--

Column 9, line 21, which reads, "soduium" should read --sodium--

Column 10, line 57, which reads "N-methyl-N-(3-fromly-3-pentanesul" should read --N-methyl-N-(3-formyl-3-pentanesul--

Signed and Sealed this

Fifteenth Day of August 1978

[SEAL]

Attest:

RUTH C. MASON
Attesting Officer

DONALD W. BANNER
Commissioner of Patents and Trademarks